United States Patent [19]

Oxford et al.

[11] Patent Number: 4,739,072

[45] Date of Patent: Apr. 19, 1988

[54] PROCESS FOR PREPARING TETRAHYDROCARBAZOLONES

[75] Inventors: Alexander W. Oxford, Royston; Colin D. Eldred, Ware; Ian H. Coates, Hertford; James A. Bell, Ware; David C. Humber, Ealing; George B. Ewan, Chalfont St. Peter, all of England

[73] Assignee: Sanofi, France

[21] Appl. No.: 888,254

[22] Filed: Jul. 23, 1986

[30] Foreign Application Priority Data

Jul. 24, 1985 [GB] United Kingdom ............... 8518741

[51] Int. Cl.$^4$ ........................................... C07D 403/00
[52] U.S. Cl. .................................................... 548/336
[58] Field of Search ........................................ 548/336

[56] References Cited

U.S. PATENT DOCUMENTS

| | | | |
|---|---|---|---|
| 3,592,824 | 7/1971 | Schut | 548/336 |
| 3,892,766 | 7/1975 | Zinnes | 548/336 |
| 4,259,345 | 3/1981 | Cross et al. | 548/336 |

FOREIGN PATENT DOCUMENTS 73849  3/1983  European Pat. Off. ............ 548/336

OTHER PUBLICATIONS

J. Chem. Soc., J. A. Ballantine, et al., 1957, 2227–2231, "Bacteria. V. Some Acylindoles".

Primary Examiner—Henry R. Jiles
Assistant Examiner—Robert C. Whittenbaugh
Attorney, Agent, or Firm—Bacon & Thomas

[57] ABSTRACT

The invention relates to a process for the preparation of a compound of general formula (I)

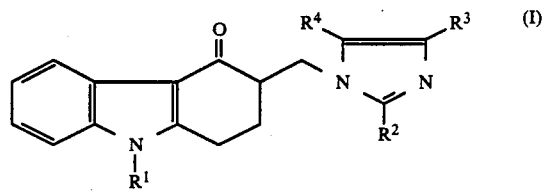

wherein $R^1$ represents a hydrogen atom or a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl, phenyl or phenyl-($C_{1-3}$)alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represent a hydrogen atom or a $C_{1-6}$ alkyl group;

or a salt or protected derivative thereof, by cyclization of a compound of general formula (II)

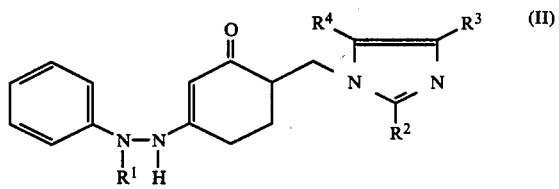

wherein $R^1$, $R^2$, $R^3$ and $R^4$ are as defined above, or a salt or a protected derivative thereof.

The compounds of formula (I) are potent and selective antagonists at "neuronal" 5-hydroxytryptamine receptors.

11 Claims, No Drawings

PROCESS FOR PREPARING TETRAHYDROCARBAZOLONES

This invention relates to improvements in or relating to a group of heterocyclic compounds. More particularly it relates to a process for their preparation.

In our British patent application No. 2153821A and European patent application No. 86300423 we describe 3-imidazolylmethyltetrahydrocarbazolones which may be represented by the general formula (I).

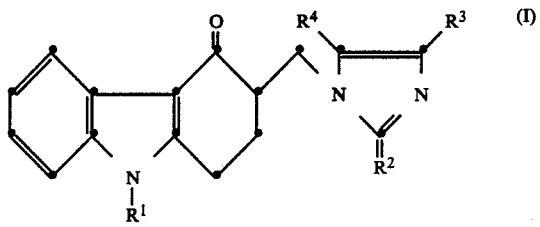

wherein $R^1$ represents a hydrogen atom or a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl, phenyl or phenyl-($C_{1-3}$) alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represents a hydrogen atom or a $C_{1-6}$ alkyl group;

and physiologically acceptable salts and solvates, e.g. hydrates, thereof. Several processes for the preparation of these compounds are also described in the above-mentioned patent applications.

The compounds of formula (I) are described in the aforementioned specifications as potent and selective antagonists at 'neuronal' 5-hydroxytryptamine (5HT) receptors, which are of use in the treatment of migraine pain and psychotic disorders such as schizophrenia. It is also stated that the compounds may be useful in the treatment of conditions such as anxiety, obesity and mania.

We have now devised a process for the preparation of the compounds of general formula (I), and salts and protected derivatives thereof in which a Fischer reaction is used as the last major chemical step in the synthesis.

According to one aspect of the present invention, therefore, we provide a process for the preparation of a compound of general formula (I) or a salt or a protected derivative thereof which comprises the step of cyclisation of a compound of general formula (II)

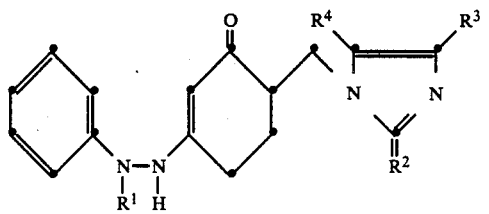

(wherein $R^1$, $R^2$, $R^3$ and $R^4$ are as defined previously) or a salt or a protected derivative thereof.

When a protected derivative of general formula (II) is used in the above process it may be for example a compound in which the carbonyl group is protected. The carbonyl protecting group may be a conventional carbonyl protecting group such as those described in "Protective Groups in Organic Chemistry" Ed. J. F. W. McOmie (Plenum Press 1973) or "Protective Groups in Organic Synthesis" by Theodora W. Greene (John Wiley & Sons 1981). Thus, for example, it may be a ketal such as a dialkyl or cyclic ketal formed with an appropriate alkylorthoformate or diol, a thioketal, a bisulphite addition complex or an enol ether.

The cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents. The acid catalyst may be, for example, an inorganic acid such as concentrated hydrochloric or sulphuric acid. (In some cases the acid catalyst may also act as the reaction solvent). In an anhydrous reaction medium, which may comprise one or more alcohols or ethers (e.g. as described above), carboxylic acids (e.g. acetic acid) or esters (e.g. ethyl acetate), the acid catalyst will generally be a Lewis acid such as boron trifluoride, zinc chloride or magnesium chloride.

Alternatively the process may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

The cyclisation reaction may conveniently be carried out at temperatures of from 20° to 200° C. preferably 50° to 125° C.

According to a particular embodiment of this process, compounds of general formula (I) may be prepared directly by the reaction of a compound of formula (III)

(wherein $R^1$ is as defined previously) or a salt thereof with a compound of formula (IV)

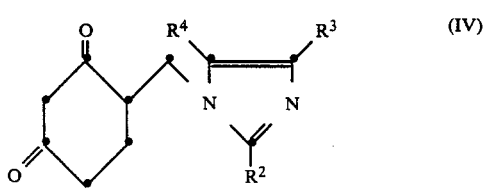

(wherein $R^2$, $R^3$ and $R^4$ are as defined previously) or a salt or protected derivative thereof using the appropriate conditions as described above.

Compounds of general formula (II) may be isolated as intermediates during the process for the preparation of compounds of general formula (I) wherein a compound of formula (III), or a salt thereof, is reacted with a compound of formula (IV) or a protected derivative thereof, in a suitable solvent such as water or an aqueous alcohol (e.g. methanol) and at a temperature of, for example, from 20° to 100° C.

A protected derivative of a compound of general formula (IV) may for example have one or both of the carbonyl groups protected, e.g. as described above for protected derivatives of formula (II). It will be appreciated that when a compound of formula (IV) is used in which the carbonyl group which reacts with the hydrazine (i.e. the group furthest from the imidazolylmethyl function) is protected, it may be necessary to remove the protecting group in order for reaction to occur with the compound of formula (III). Deprotection may be effected by conventional procedures, for example as described hereinafter. If desired, deprotection may be effected in situ.

The compounds of formula (IV) may be prepared by reacting an imidazole of formula (V)

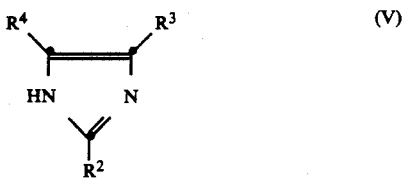

(V)

(wherein $R^2$, $R^3$ and $R^4$ are as defined previously) or a salt thereof with a compound of formula (VI)

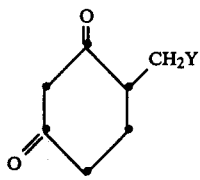

(VI)

(wherein Y represents a leaving atom or group, for example a halogen atom or the group $-N^+(CH_3)_3$ which will have an associated anion such as a halide ion, e.g. $I^-$) or a protected derivative thereof e.g. a corresponding compound in which the carbonyl group at the 3-position is protected as described for compounds of formula (IV) (for example as an enol ether such as the methyl enol ether).

The reaction is conveniently effected in a suitable solvent such as water, an amide, e.g. dimethylformamide, a ketone, e.g. acetone or an ether, e.g. dioxan, and at a temperature of from 20° to 150° C.

The compounds of formula (VI) wherein Y represents the group $N^+(CH_3)_3I^-$ may be prepared by a Mannich reaction using a cyclohexane-1,3-dione derivative in which one of the carbonyl groups is protected (for example as the methyl enol ether) followed by methylation. Thus the protected dione may be reacted with formaldehyde and dimethylamine. More conveniently the cyclohexane-1,3-dione, in the form of an enolate, may be reacted with Eschenmoser's salt ($CH_2=N^+(CH_3)_2I^-$), followed by reaction with a methylating agent such as methyl iodide.

A compound of formula (VI) in which Y represents a halogen atom may be prepared for example by reacting cyclohexane-1,3-dione with formaldehyde in the presence of a base to give a compound of formula (VI) in which Y represents a hydroxy group, and reacting this with a halogenating agent such as phosphorus tribromide.

Where it is necessary and/or desired to effect deprotection of a compound at any stage in the reaction sequence, this may be effected using conventional techniques such as those described in 'Protective Groups in Organic Chemistry' Ed. J. F. W. McOmie (Plenum Press, 1973) or 'Protective Groups in Organic Synthesis' by Theodora W Greene (John Wiley & Sons 1981). Thus, a ketal such as an alkyleneketal group may be removed by treatment with a mineral acid such as hydrochloric acid. A thioketal group may be cleaved by treatment with a mercuric salt, e.g. mercuric chloride, in a suitable solvent, such as ethanol. An enol ether may be hydrolysed in the presence of an aqueous acid, e.g. dilute sulphuric acid or dilute hydrochloric acid.

The compounds of formula (I) may be converted into their physiologically acceptable salts according to conventional methods. Thus, for example, the free base of general formula (I) may be treated with an appropriate acid, preferably with an equivalent amount, in a suitable solvent (e.g. aqueous ethanol).

Preferred compounds which may be prepared by the process of the present invention are compounds of general formula (I) wherein $R^1$ represents a hydrogen atom or a $C_{1-10}$ alkyl, $C_{3-7}$ cycloalkyl, $C_{3-6}$ alkenyl, phenyl or phenyl-($C_{1-3}$)-alkyl group, and $R^2$, $R^3$ and $R^4$ are as previously defined, and physiologically acceptable salts and solvates e.g. hydrates thereof.

Preferred compounds which may be prepared according to the process of the present invention are:
1,2,3,9-tetrahydro-3-[(2-methyl-1H-imidazol-1-yl)methyl]-9-(2-propenyl)-4H-carbazol-4-one;
9-cyclopentyl-1,2,3,9-tetrahydro-3-[(2-methyl-1H-imidazol-1-yl)methyl]-4H-carbazol-4-one; and
1,2,3,9-tetrahydro-9-(1-methylethyl)-3-[(2-methyl-1H-imidazol-1-yl)methyl]-4H-carbazol-4-one and their physiologically acceptable salts and solvates.

A particularly preferred compound is 1,2,3,9-tetrahydro-9-methyl-3-[(2-methyl-1H-imidazol-1-yl)methyl]-4H-carbazol-4-one, and the physiologically acceptable salts and solvates (e.g. hydrates) thereof. A preferred form of this compound is the hydrochloride dihydrate.

The following Preparations and Examples illustrate the invention. All temperatures are in °C.

Chromatography was carried out either in the conventional manner using silica gel (Merck, Kieselgel 60, Art. 7734 or 7747) or by flash chromatography (W. C. Still, M. Kahn and A. Mitra, *J. Org. Chem.* 1978, 43, 2933) on silica (Merck 9385) and thin layer chromatography (t.l.c.) on silica (Macherly-Nagel, Polygram) except where otherwise stated. The following abbreviations define the eluent used for chromatography and t.l.c.

| A | Dichloromethane-ethanol-0.88 ammonia | 89:10:1 |
| B | Dichloromethane-ethanol-0.88 ammonia | 95:5:1 |
| C | Dichloromethane-ethanol-0.88 ammonia | 200:10:1 |
| D | Ethyl acetate-methanol | 19:1 |

Intermediates were checked for purity by t.l.c. employing u.v. light for detection and spray reagents such as potassium permanganate (KMnO$_4$) or a solution of iodoplatinic acid (IPA).

Proton ($^1$H) nuclear magnetic resonance (n.m.r.) spectra were obtained either at 90 MHz using a Varian EM 390 instrument or at 250 MHz using a Bruker Am or WM 250 instrument. s=singlet, d=doublet, t=triplet, m=multiplet, q=quartet, and br=broad.

INTERMEDIATE 1

6-[(Dimethylamino)methyl]-3-methoxy-2-cyclohexen-1-one maleate n-Butyllithium (1.55M in hexane, 32.3 ml) was added to a stirred solution of dry diisopropylamine (7.0 ml) in dry tetrahydrofuran (60 ml) at −70° under nitrogen, and stirring was continued for 10 min. A solution of 3-methoxy-2-cyclohexen-1-one (5.0 g) in dry THF (10 ml) was added dropwise over 10 min, and stirring was continued at −70° to −60° for 40 min. The mixture was transferred by a double ended needle to a second flask containing a stirred suspension of N,N-dimethylmethylene ammonium iodide (Eschenmoser's salt) (13.9 g) in dry THF (40 ml) at −60°, and the mixture was allowed to warm to 0° with stirring over 4 h, and allowed to stand at room temperature overnight. The mixture was poured into 8% aqueous sodium bicarbonate (200 ml), further basified with 2N sodium hydroxide (100 ml), saturated with sodium chloride, and extracted with ether (4×200 ml). The organic layers were washed with brine, dried (MgSO$_4$) and evaporated to give an oil (7.65 g). Purification by short path chromatography (A) gave the free base as an oil (3.94 g). A portion of the oil (187 mg) was dissolved in methanol (1 ml), maleic acid (124 mg) in methanol (1 ml) was added and the solution was diluted with dry ether (70 ml), giving a precipitate, which was filtered off, washed with ether and dried (in vacuo at room temperature) to present the title compound as a solid (283 mg), m.p. 132°–134°.

INTERMEDIATE 2

3-Methoxy-6-[(2-methyl-1H-imidazol-1-yl)methyl]-2-cyclohexen-1-one maleate

Iodomethane (1.27 ml) was added to a stirred solution of Intermediate 1 as the base (3.7 g) in dry N,N-dimethylformamide (80 ml) at room temperature under nitrogen, and stirring was continued at room temperature for 25 min. 2-Methylimidazole (8.4 g) was added, and the mixture was heated at 80° for 4 h. The mixture was poured into brine (250 ml) and extracted with ethyl acetate (3×250 ml). The organic layers were washed with brine (3×250 ml) and the combined aqueous layers further extracted with ethyl acetate (3×400 ml). The combined organic layers were dried (MgSO$_4$) and evaporated to give a semi-solid (10.5 g). Purification by flash chromatography (A) gave the product as an oil which slowly crystallised (3.60 g). A sample (165 mg) was dissolved in methanol (0.5 ml), and maleic acid (91 mg) was added. Addition of dry ether (25 ml) gave a precipitate which was filtered off, washed with dry ether and dried (in vacuo at room temperature) to present the title compound as a solid (192 mg), m.p. 134.5°–135.5°.

EXAMPLE 1

1,2,3,9-Tetrahydro-9-methyl-3-[(2-methyl-1H-imidazol-1-yl)methyl]-4H-carbazol-4-one (i) 6-[(2-Methyl-1H-imidazol-1-yl)methyl]-3-(2-methyl-2-phenylhydrazino)-2-cyclohexen-1-one dihydrochloride Intermediate 2 as the base (1.1 g) was dissolved in water (30 ml), 2N hydrochloric acid (5 ml) was added and the mixture was stirred at room temperature under nitrogen for 3.5 h. 1-Methyl-1-phenylhydrazine (0.59 ml) was added, and stirring was continued at room temperature for 18 h. The mixture was poured into 8% aqueous sodium bicarbonate (20 ml) and extracted with ethyl acetate (3×50 ml), the organic layers were washed with brine, dried (MgSO$_4$) and evaporated to give an oil (0.97 g). Purification by flash chromatography (A) gave the product as an oil (272 mg). The aqueous layers from above were acidified with 2N hydrochloric acid (10 ml), 1-methyl-1-phenylhydrazine (1.2 ml) was added, and the mixture was stirred at room temperature for 16 h (pH ca. 3). Further 1-methyl-1-phenylhydrazine (1.2 ml) was added, and stirring was continued overnight (ca. 6). The mixture was basified with aqueous sodium bicarbonate (8%, 50 ml) and extracted with ethyl acetate (3×50 ml); the organic layers were washed with brine, dried (MgSO$_4$) and evaporated to give an oil (2.4 g). Purification by flash chromatography (A) gave a second crop of the product as an oil (0.7 g). The oil was dissolved in warm ethyl acetate and acidified with ethereal hydrogen chloride to give a precipitate. The precipitate was filtered off, washed with ethyl acetate and dried (in vacuo at 60°) to present the title compound as a solid (0.42 g), m.p. 147°–150°.

(ii) 1,2,3,9-Tetrahydro-9-methyl-3-[(2-methyl-1H-imidazol-1-yl)methyl]-4H-carbazol-4-one The product of Stage (i) as the base (180 mg) was heated at 85° with dry zinc chloride (1.8 g) in glacial acetic acid (5 ml) for 5 h 20 min. The mixture was cooled, poured into 2N aqueous sodium hydroxide (60 ml) and water (40 ml), and extracted with ethyl acetate (3×50 ml). The organic layers were washed with water and brine, dried (MgSO$_4$) and evaporated to give a solid (141 mg). Purification by flash chromatography (B) gave the product as a solid (86 mg) m.p. 216°–218°. Recrystallisation from methanol gave the title compound (59 mg), m.p. 227.5°–228.5°.

Analysis Found: C, 72.45; H, 6.6; N, 14.1. C$_{18}$H$_{19}$N$_3$O.0.31H$_2$O requires: C, 72.3; H, 6.4; N, 14.05%.

The product was shown by n.m.r. and t.l.c. to be identical with the product of Example 1(a) in British Patent Application No. 2153821A (as the free base).

EXAMPLE 2

(i)

6-[(2-methyl-1H-imidazol-1-yl)methyl]-3-[2-phenyl-2-(2-propenyl)hydrazino]-2-cyclohexen-1-one A solution of Intermediate 2 (as the free base) (500 mg) in water (15 ml) and 2N hydrochloric acid (2.5 ml) was stirred at room temperature for 2.5 h. 1-Phenyl-1-(2-propenyl)hydrazine (505 mg) was added and stirring continued for 4 days. The solution was poured into 8% sodium bicarbonate solution (80 ml) and extracted with dichloromethane (3×40 ml). The combined extracts were dried (MgSO$_4$), filtered and evaporated to give a gum (ca. 1.0 g). Short path column chromatography (C)

gave the title compound as a foam (235 mg) T.l.c. (C), Rf 0.30.

(ii)

1,2,3,9-Tetrahydro-3-[(2-methyl-1H-imidazol-1-yl)methyl]-9-(2-propenyl)-4H-carbazol-4-one A mixture of the product of Stage (i) (100 mg) and zinc chloride (491 mg) in glacial acetic acid (2 ml) was heated at reflux for 2 h. The mixture was poured into 2N sodium carbonate solution (30 ml) and extracted with dichloromethane (3×15 ml). The combined extracts were dried (MgSO₄), filtered and evaporated to give an oil (95 mg). Column chromatography (D) gave the title compound as a solid (54 mg) m.p. 132°. This was shown by n.m.r. and t.l.c. to be identical to the product of Example 6 of UK Patent Application No. 2153821A (as the free base).

EXAMPLE 3

(i)

3-[2-(1-methylethyl)-2-phenylhydrazino]-6-[(2-methyl-1H-imidazol-1-yl)methyl]-2-cyclohexen-1-one A solution of Intermediate 2 as the free base (500 mg) in water (15 ml) and 2N hydrochloric acid (2.5 ml) was stirred at room temperature for 2.5 h. 1-(1-Methylethyl)-1-phenylhydrazine (511 mg) was added and stirring continued for 4 days. The solution was poured into 8% sodium bicarbonate solution (80 ml) and extracted with dichloromethane (3×40 ml). The combined extracts were dried (MgSO₄), filtered and evaporated to give a gum (ca 600 mg). Short path column chromatography (C) gave the title compound as a foam (200 mg). T.l.c. (C), Rf 0.30.

(ii)

1,2,3,9-Tetrahydro-9-(1-methylethyl)-3-[(2-methyl-1H-imidazol-1-yl)methyl]-4H-carbazol-4-one A mixture of the product of Stage (i) (100 mg) and zinc chloride (491 mg) in glacial acetic acid (2 ml) was heated at reflux for 2 h. The mixture was poured into 2N sodium carbonate solution (30 ml) and extracted with dichloromethane (3×15 ml). The combined extracts were dried (MgSO₄), filtered and evaporated to give an oil (95 mg). Column chromatography (D) gave the title compound as a foam (53 mg). T.l.c. SiO₂(impregnated with triethyl-amine, eluent D), Rf 0.21. This product was shown by n.m.r. and t.l.c. to be identical with the product of Example 9 of UK Patent Application No. 2153821A (as the free base).

We claim:

1. A process for the preparation of a compound of formula (I)

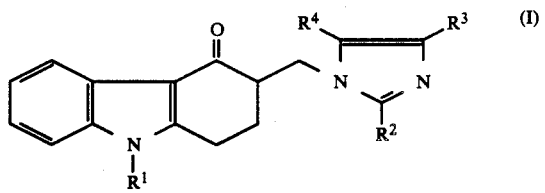

wherein
R¹ represents a hydrogen atom or a C₁₋₁₀ alkyl, C₃₋₇ cycloalkyl, C₃₋₇ cycloalkyl-(C₁₋₄)alkyl, C₃₋₆ alkenyl, C₃₋₁₀ alkynyl, phenyl or phenyl-(C₁₋₃)alkyl group, and one of the groups represented by R², R³ and R⁴ is a hydrogen atom or a C₁₋₆ alkyl, C₃₋₇ cycloalkyl, C₂₋₆ alkenyl or phenyl-(C₁₋₃)alkyl group and each of the other two groups, which may be the same or different, represent a hydrogen atom or a C₁₋₆ alkyl group;
or a salt or protected derivative thereof,
which comprises the step of cyclisation in aqueous or non-aqueous media in the presence of an acid catalyst of a compound of formula (II)

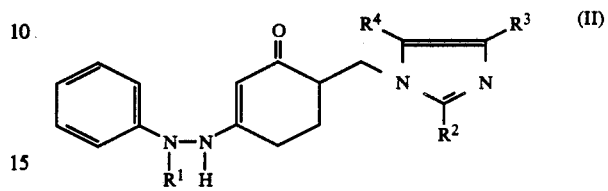

wherein R¹, R², R³ and R⁴ are as defined above, or a salt or a protected derivative thereof.

2. A process as claimed in claim 1, wherein the compound of formula (I) is produced in the form of a protected derivative and the protecting group or groups are subsequently removed to produce the compound of formula (I) and/or the compound of formula (I) is produced in the form of the free base and the free base is subsequently converted into a salt.

3. A process as claimed in claim 1 wherein said anhydrous reaction medium comprises one or more alcohols, ethers, carboxylic acids or esters.

4. A process as claimed in claim 1 wherein the reaction between the compound of formula (III) or a salt thereof and the compound of formula (IV) or a protected derivative thereof is carried out in water or an aqueous alcohol at a temperature from 20° to 100° C.

5. A process as claimed in claim 1, for the production of a compound of formula (I) in which R¹ represents a hydrogen atom or a C₁₋₁₀ alkyl, C₃₋₇ cycloalkyl, C₃₋₆ alkenyl, phenyl or phenyl-(C₁₋₃)-alkyl group, and R², R³ and R⁴ are as defined in claim 1 or a physiologically acceptable salt or solvate thereof.

6. A process as claimed in claim 1 for the production of a compound selected from:

1,2,3,9-tetrahydro-3-[(2-methyl-1H-imidazol-1-yl)methyl]-9-(2-propenyl)-4H-carbazol-4-one;

9-cyclopentyl-1,2,3,9-tetrahydro-3-[(2-methyl-1H-imidazol-1-yl)methyl]-4H-carbazol-4-one;

1,2,3,9-tetrahydro-9-(1-methylethyl)-3-[(2-methyl-1H-imidazol-1-yl)methyl]-4H-carbazol-4-one;

and physiologically acceptable salts and solvates thereof.

7. A process as claimed in claim 1 for the production of 1,2,3,9-tetrahydro-9-methyl-3-[(2-methyl-1H-imidazol-1-yl)methyl]-4H-carbazol-4-one or a physiologically acceptable salt or solvate thereof.

8. A process for the preparation of a compound of formula (I)

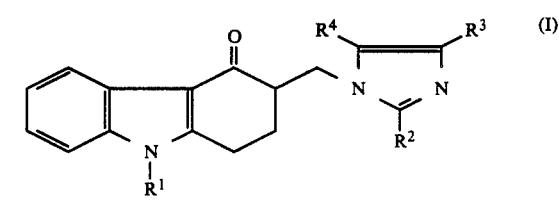

wherein
R¹ represents a hydrogen atom or a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl, phenyl or phenyl-($C_{1-3}$)alkyl group, and one of the groups represented by R², R³ and R⁴ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represent a hydrogen atom or a $C_{1-6}$ alkyl group;

or a salt or protected derivative thereof, which comprises the step of cyclisation in an adhydrous reaction media in the presence of a Lewis acid of a compound of formula (II)

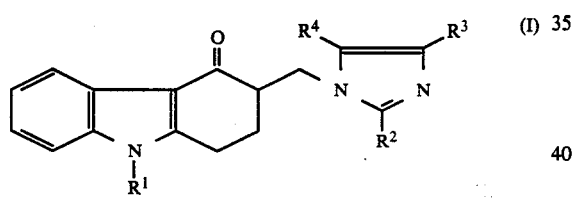
(II)

wherein R¹, R², R³ and R⁴ are as defined above, or a salt or a protected derivative thereof.

9. A process for the preparation of a compound of formula (I)

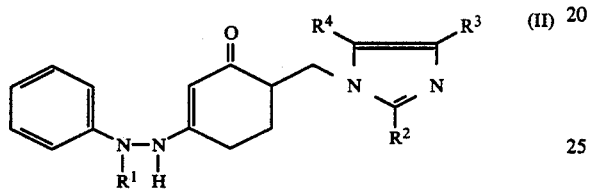
(I)

wherein
R¹ represents a hydrogen atom or a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl, phenyl or phenyl-($C_{1-3}$)alkyl group, and one of the groups represented by R², R³ and R⁴ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represent a hydrogen atom or a $C_{1-6}$ alkyl group;

or a salt or protected derivative thereof, which comprises directly reacting a compound of formula (III)

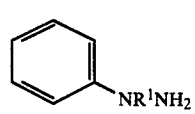
(III)

wherein R¹ is as defined above or a salt thereof with a compound of formula (IV)

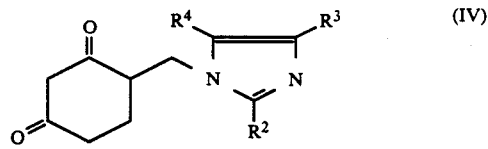
(IV)

wherein R², R³, and R⁴ are as defined above, or a salt or protected derivative thereof.

10. A process for the preparation of a compound of formula (I)

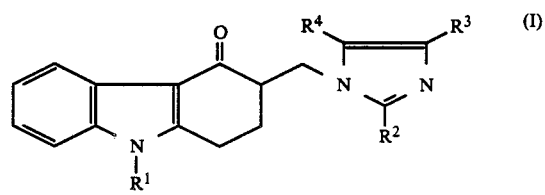
(I)

wherein
R¹ represents a hydrogen atom or a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl, phenyl or phenyl-($C_{1-3}$)alkyl group, and one of the groups represented by R², R³ and R⁴ is a hydrogen atom or a $C_{1-6}$ alkyl, $C_{3-7}$ cycloalkyl, $C_{2-6}$ alkenyl or phenyl-($C_{1-3}$)alkyl group and each of the other two groups, which may be the same or different, represent a hydrogen atom or a $C_{1-6}$ alkyl group;

or a salt or protected derivative thereof, which comprises reacting a compound of formula (III)

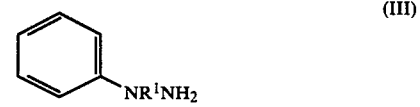
(III)

wherein R¹ is as defined above, or a salt thereof with a compound of formula (IV)

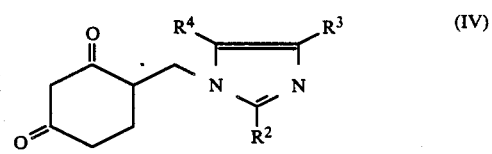
(IV)

wherein R², R³, and R⁴ are as defined above or a salt or protected derivative thereof to yield a compound having a formula (II)

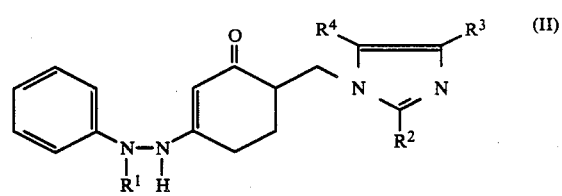
(II)

wherein R¹, R², R³ and R⁴ are as defined above, or a salt or protected derivative thereof and cyclising compound II.

11. A process as claimed in claim 1 wherein the reaction is carried out in a temperature range of from 20°–200° C.

* * * * *

UNITED STATES PATENT AND TRADEMARK OFFICE
CERTIFICATE OF CORRECTION

PATENT NO. : 4,739,072

DATED : April 19, 1988

INVENTOR(S) : OXFORD et al

It is certified that error appears in the above-identified patent and that said Letters Patent is hereby corrected as shown below:

On the cover page, at item [73] Assignee: cancel, "Sanofi, France"

and insert --Glaxo Group Limited, London, England--.

Signed and Sealed this

Twentieth Day of September, 1988

Attest:

DONALD J. QUIGG

Attesting Officer      Commissioner of Patents and Trademarks

UNITED STATES PATENT AND TRADEMARK OFFICE
CERTIFICATE OF CORRECTION

PATENT NO. : 4,739,072

DATED : April 19, 1988

INVENTOR(S) : Alexander W. OXFORD et al

It is certified that error appears in the above-identified patent and that said Letters Patent is hereby corrected as shown below:

Claim 3, line 1, delete "1" and insert —8—.

Claim 4, line 1, delete "1" and insert —10—.

Signed and Sealed this

Twenty-seventh Day of March, 1990

Attest:

JEFFREY M. SAMUELS

*Attesting Officer*     *Acting Commissioner of Patents and Trademarks*